(12) United States Patent
Morin et al.

(10) Patent No.: US 11,883,280 B2
(45) Date of Patent: Jan. 30, 2024

(54) PROSTHETIC LEAFLETS FOR VALVE REPLACEMENT

(71) Applicant: St. Jude Medical, Cardiology Division, Inc., St. Paul, MN (US)

(72) Inventors: Kristen T. Morin, St. Paul, MN (US); Jay Reimer, Saint Paul, MN (US); Keith T. High, White Bear Lake, MN (US); Kristopher Henry Vietmeier, Monticello, MN (US); Tracee Eidenschink, Wayzata, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 325 days.

(21) Appl. No.: 17/187,063

(22) Filed: Feb. 26, 2021

(65) Prior Publication Data
US 2021/0267756 A1 Sep. 2, 2021

Related U.S. Application Data

(60) Provisional application No. 62/982,903, filed on Feb. 28, 2020.

(51) Int. Cl.
*A61F 2/24* (2006.01)
*A61L 31/02* (2006.01)
(Continued)

(52) U.S. Cl.
CPC .............. *A61F 2/2409* (2013.01); *A61F 2/24* (2013.01); *A61F 2/2412* (2013.01);
(Continued)

(58) Field of Classification Search
CPC ........ A61F 2/24; A61F 2/2409; A61F 2/2415; A61F 2/2412; A61L 31/022; A61L 31/10; A61L 31/146; A61L 2400/18; B32B 15/00; B32B 15/04; B32B 15/08; B32B 27/281; B32B 27/283; B32B 27/302; B32B 27/304; B32B 27/32; B32B 27/365; B32B 27/40
See application file for complete search history.

(56) References Cited

U.S. PATENT DOCUMENTS

2008/0243245 A1* 10/2008 Thambar .................. A61F 2/24
623/2.11
2009/0132035 A1 5/2009 Roth et al.
(Continued)

FOREIGN PATENT DOCUMENTS

EP 2379322 B1 6/2018

OTHER PUBLICATIONS

Partial International Search Report for Application No. PCT/US2021/019826, 12 pages.
(Continued)

*Primary Examiner* — Dinah Baria
(74) *Attorney, Agent, or Firm* — SLEMAN & LUND LLP

(57) ABSTRACT

A prosthetic heart valve includes a support structure and a valve assembly disposed within the support structure, the valve assembly including a plurality of leaflets. Each leaflet is formed from a predetermined leaflet material. Some leaflet materials include a metal body with a plurality of openings. The metal body may be coated with a polymer. Other leaflet materials include natural mammalian tissue subjected to a plastination preservation process.

13 Claims, 10 Drawing Sheets

(51) Int. Cl.
 A61L 31/10 (2006.01)
 A61L 31/14 (2006.01)
(52) U.S. Cl.
 CPC .......... *A61F 2/2415* (2013.01); *A61F 2/2463* (2013.01); *A61L 31/022* (2013.01); *A61L 31/10* (2013.01); *A61L 31/146* (2013.01); *A61L 2400/18* (2013.01)

(56) References Cited

U.S. PATENT DOCUMENTS

| | | | | |
|---|---|---|---|---|
| 2012/0245706 | A1* | 9/2012 | Alavi | A61F 2/90 623/23.72 |
| 2014/0180399 | A1 | 6/2014 | Alavi et al. | |
| 2016/0250024 | A1* | 9/2016 | Hill | A61F 2/2475 623/1.24 |
| 2018/0043058 | A1 | 2/2018 | Kheradvar | |

OTHER PUBLICATIONS

Plain weave, Encyclopaedia Brittanica, Dec. 17, 2010, <https://www.britannica.com/technology/plain-weave> accessed on Oct. 11, 2019.

Watson, Kate Heintz et al., Textiles and Clothing, 1907, Home Economics Association, p. 77.

Difference between Warp Rib Weave and Weft Rib Weave, Define Textile, 2019, <http://www.definetextile.com/2013/05/difference-between-warp-rib-weave-and.html>, accessed on Oct. 23, 2019.

Twill weave, 2019, https://www.dictionary.com/browse/twill-weave, accessed on Oct. 11, 2019.

What is a Herringbone Weave?, Shirts of Holland B.V., 2019, https://sleeve7.com/blog/what-is-a-herringbone-weave/, accessed on Oct. 11, 2019.

Basic Weaves, Cotton Incorporated, 2019, https://www.cottonworks.com/topics/sourcing-manufacturing/weaving/the-art-of-weaving-basic-weaves/, accessed on Oct. 11, 2019.

Leno Weaves, Serial 512. Ed. 1., International Textbook Co., https://www2.cs.arizona.edu/patterns/weaving/monographs/ics512.pdf, accessed on Oct. 11, 2019.).

Bedford Cords, TextileSchool4U.Blogspot.com, 2013, http://textileschool4u.blogspot.com/2013/12/bedford-cords.html, accessed on Oct. 11, 2019.

Honeycomb, The Free Dictionary, https://www.thefreedictionary.com/waffle+weave, accessed on Oct. 11, 2019.

Adam Augustyn, Weaving, 2008, https://www.britannica.com/technology/weaving#ref290551, accessed on Oct. 11, 2019.

Tapestry Weaving Basics, 2019, https://www.mirrixlooms.com/pages/ tapestryweaving-basics, accessed on Oct. 11, 2019.

Double Cloth, Mar. 20, 2019, https://en.wikipedia.org/wiki/Double_cloth#cite_ref-text_2-0 https://en.wikipedia.org/wiki/Double_cloth, accessed on Oct. 11, 2019.

Rib-Knit, Merriam-Webster, 2019, https://www.merriam-webster.com /dictionary/rib-knit, accessed on Oct. 11, 2019.

Warp knitting, Sep. 15, 2019, https://en.wikipedia.org/wiki/ Warp_knitting, accessed on Oct. 11, 2019.

https://www.thefreedictionary.com/single-knit ; accessed Jul. 24, 2020.

https://www.thefreedictionary.com/double-knit ; accessed Jul. 24, 2020.

* cited by examiner

PROSTHETIC LEAFLETS FOR VALVE REPLACEMENT

CROSS REFERENCE TO RELATED APPLICATION

This application claims the priority from U.S. Provisional Patent Application No. 62/982,903, filed on Feb. 28, 2020, the disclosure of which is incorporated herein by reference.

BACKGROUND OF THE DISCLOSURE

The present disclosure relates to prosthetic heart valves, and to materials for use in prosthetic heart valves. More particularly, the present disclosure relates to alternative materials that may be used for leaflet materials in prosthetic heart valves.

Prosthetic heart valves, including surgical heart valves and collapsible heart valves intended for transcatheter aortic valve replacement/repair ("TAVR") or transcatheter mitral valve replacement/repair ("TMVR"), are well known in the patent literature. Surgical or mechanical heart valves may be sutured into a native annulus of a patient during an open-heart surgical procedure, for example. Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

Leaflets, cuffs and valve assemblies for prosthetic heart valves may be derived from various natural tissues, including various animal tissues, or may be a combination of natural tissues that have been chemically treated or "fixed." However, there is variability within natural tissue that can lead to challenges in properly selecting and manufacturing such heart valves and leaflets. Leaflets made from animal tissue, such as porcine tissue, have been shown to calcify to varying degrees in clinical use, limiting their lifespans. Over an extended patient lifespan, such biological leaflets may eventually erode or tear, creating a need for further surgical intervention or an additional valve replacement.

Additionally, the thickness of the leaflet material is important due to the growing prevalence of transcatheter heart valves including TAVR and TMVR. Thinner materials enable the prosthetic heart valve to be collapsed to a smaller size for delivery to the patient's heart percutaneously.

Therefore, there is a need for further improvements to leaflet materials to address the current shortcomings of leaflets made from animal tissue. An ideal material for use in prosthetic heart valve leaflets will be resistant to calcification and have a long functional life. Among other advantages, the present invention may address one or more of these needs.

BRIEF SUMMARY OF THE DISCLOSURE

The disclosure herein describes multiple embodiments of a leaflet material that can be used in current and future prosthetic heart valves, including surgically implanted mechanical heart valves and transcatheter heart valves. One such prosthetic heart valve may include a support structure; and a valve assembly disposed within the support structure, the valve assembly including a plurality of leaflets, wherein each leaflet is formed from a composite material, the composite material including a metal substrate having a plurality of openings and a polymer coated on the metal substrate.

Another such prosthetic heart valve may include a support structure; and a valve assembly disposed within the support structure, the valve assembly including a plurality of leaflets, wherein each leaflet is formed from a metal body having a plurality of openings, the metal body including a fine wire that is woven, knitted or braided to form a mesh Still another prosthetic heart valve may include a support structure; and a valve assembly disposed within the support structure, the valve assembly including a plurality of leaflets, wherein each leaflet is formed from natural tissue that has been subjected to a plastination preservation process.

BRIEF DESCRIPTION OF THE DRAWINGS

This disclosure may be best understood by reference to the following description taken in conjunction with the accompanying drawing figures, in which.

DETAILED DESCRIPTION

As used herein, the term "inflow," when used in connection with a prosthetic heart valve, refers to the end of the heart valve through which blood enters when the valve is functioning as intended, whereas the term "outflow," when used in connection with a prosthetic heart valve, refers to the end of the heart valve through which blood exits when the valve is functioning as intended. Also as used herein, the terms "generally," "substantially," "approximately," and "about" are intended to mean that slight deviations from absolute are included within the scope of the term so modified. When used to indicate relative locations within the prosthetic heart valve, the terms "longitudinal" and "vertical" are to be taken as the direction of the axis extending between the inflow end and the outflow end of the stent of the heart valve, along the direction of intended blood flow; the term "flow direction" is to be taken as the direction from the inflow end to the outflow end of the stent of the heart valve; and the terms "above," "below," "high," and "low" are to be taken as relative to the inflow end of the stent. "Above" and "high" are to be understood as relatively farther from the inflow end of the stent in the direction of intended blood flow, and "below" and "low" are to be understood as relatively closer to the inflow end of the stent in the direction of intended blood flow. When used to indicate relative locations within the prosthetic heart valve, the term "circumferential" is to be taken as the direction of rotation about the longitudinal axis of the stent. Like reference numbers refer to similar or identical elements throughout.

Figure 1:
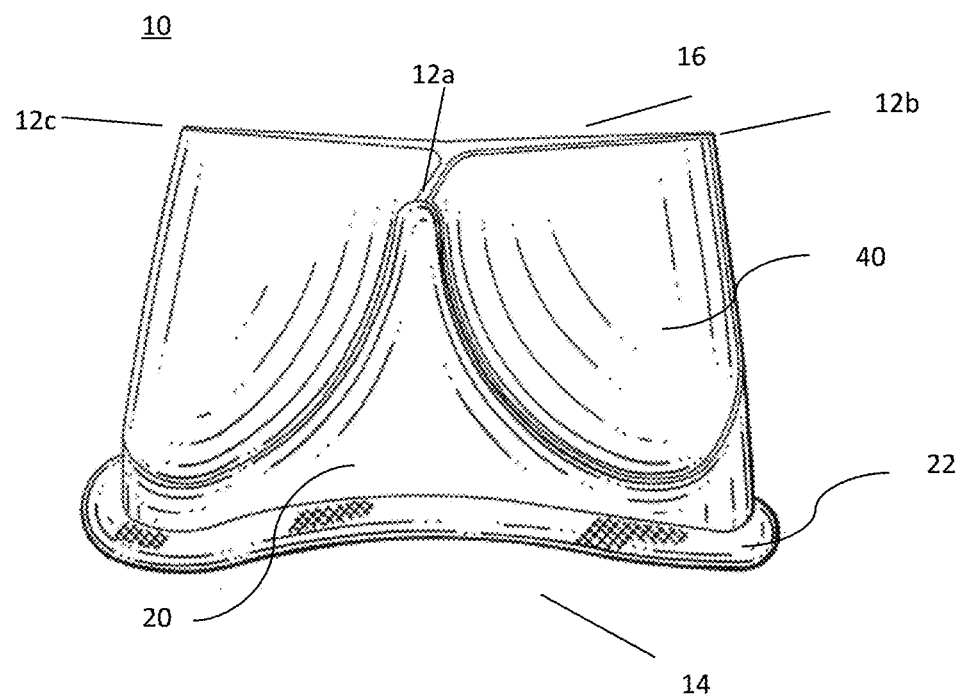
FIG. 1 is a perspective view of a surgical heart valve according to the prior art.

An illustrative embodiment of a surgical heart valve 10 ("SHV") is shown in FIG. 1. SHV 10 may be surgically implanted into a patient to replace a native heart valve that may be malfunctioning, such as the aortic valve, mitral valve, pulmonary valve or the tricuspid valve. The SHV 10 may be sutured into a native valve annulus, such as during an open-heart surgical procedure. The SHV 10 may have a non-collapsible frame (not shown) having a generally annular shape. The frame is typically made from a biologically compatible metal, such as titanium, Elgiloy® or MP35N®, or a biologically compatible polymer, such as PEEK or acetal. Since the valve of the illustrative embodiment is a tricuspid valve (e.g., for use in replacing a patient's aortic valve), the frame has three commissure portions or regions 12a, 12b and 12c that are equally spaced from one another around the circumference of the frame. Each commissure portion stands up from the annularly continuous base of the frame, and they collectively support and/or serve as attachment points for a plurality of prosthetic heart leaflets 40. Although SHV 10 is shown with three commissure portions, 12a-c for supporting a three-leaflet valve assembly, it should be understood that the SHV could include more or fewer commissure portions for supporting a corresponding number of prosthetic leaflets. The base of the frame may include a blood-inflow edge 14 that is scalloped as one proceeds around the frame to approximately match the natural scallop of the native valve annulus. The frame also includes an annularly continuous blood-outflow edge 16, which merges with and becomes part of each commissure portion 12a-c. The inflow edge 14, outflow edge 16 and flexibility of the frame are designed to help insure proper opening and coaptation of the leaflets 40 of the prosthetic heart valve during use. The prosthetic leaflets 40 may be formed from a biological material, such as bovine pericardium, or from any of the engineered leaflet materials discussed herein.

The frame may be covered by a fabric covering (not shown), particularly over each commissure portion 12a-c. One example of an appropriate covering fabric is reemay fabric, which is a spun form of polyester. A ring 20, such as a silicone ring, may be positioned around the outside of the inflow edge 14 of the frame. The entire frame and ring 20 may be completely covered inside and out by a further fabric layer. Subsequently, a layer of tissue 22 may be applied over the fabric layer, including both inside and outside of the frame and over the ring Tissue layer 22 may be formed of any mammalian tissue, and in particular any mammalian pericardium tissue, such as porcine, equine or bovine pericardium. In the completed SHV 10, the covered ring 20 serves as a sewing cuff for sewing the prosthetic heart valve into the native valve annulus of the patient.

Figure 2:
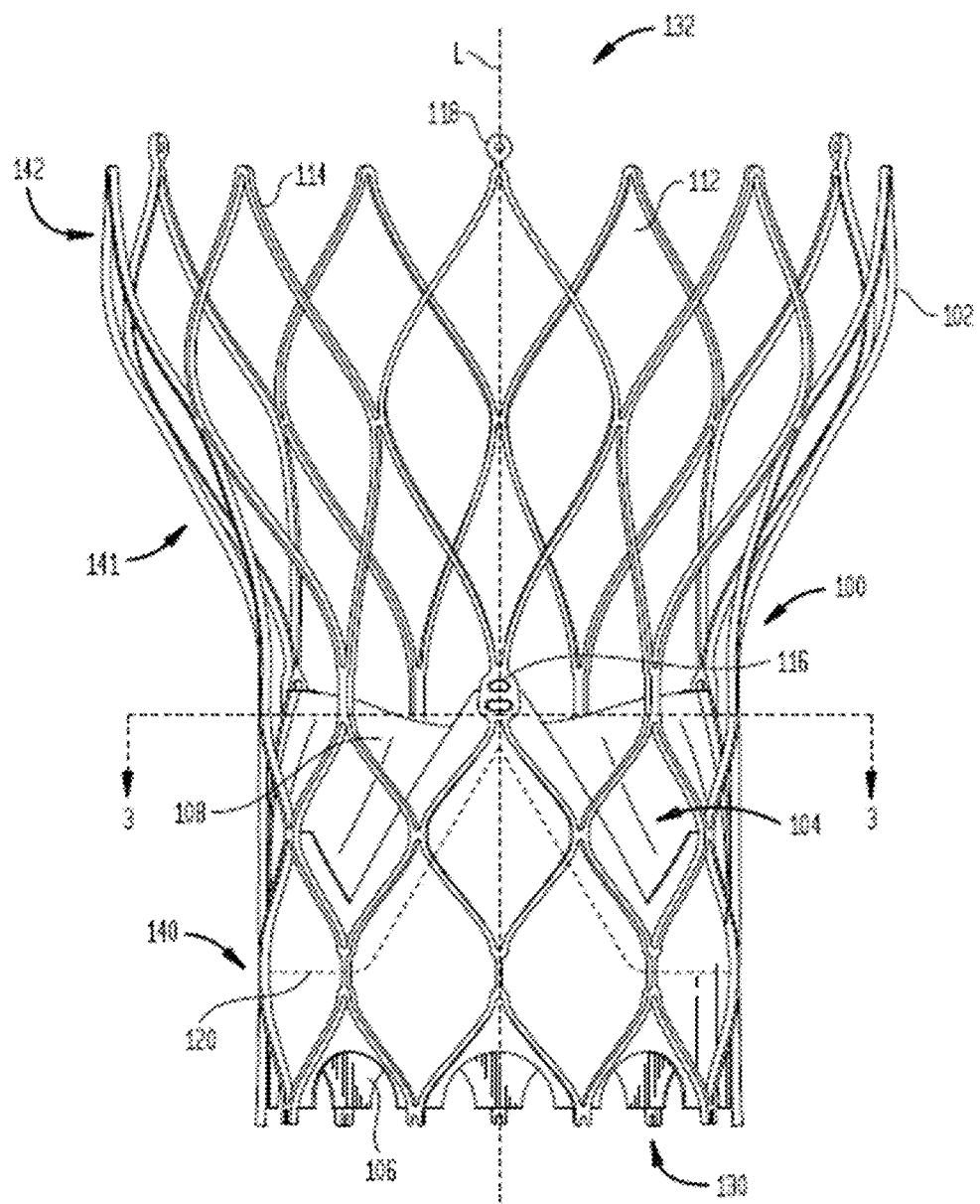
FIG. 2 is a side view of a collapsible stent-supported prosthetic heart valve according to the prior art, in an expanded condition.

FIG. 2 shows one embodiment of a collapsible stent-supported prosthetic heart valve 100 according to the prior art, the prosthetic heart valve being shown in an expanded condition. Prosthetic heart valve 100 is designed to replace the function of the native aortic valve of a patient, and includes a stent 102 which serves as a frame for the valve elements. Stent 102 extends along a lengthwise or longitudinal axis L from an inflow or annulus end 130 to an outflow or aortic end 132, and includes an annulus section 140 adjacent inflow end 130 and an aortic section 142 adjacent outflow end 132. Annulus section 140 may be in the form of a cylinder having a substantially constant diameter along its length, and may have a relatively small transverse cross-section in the expanded condition in comparison to the transverse cross-section of aortic section 142. A transition section 141 may taper outwardly from annulus section 140 to aortic section 142. Each of the sections of stent 102 includes a plurality of cells 112 formed by interconnected struts 114. Each cell 112 may include four struts 114 connected together generally in a diamond shape so as to form a cell that may be readily collapsed and expanded. It will be appreciated that a smaller or larger number of struts may be used to form cells having a different shape. The cells 112 in each section of stent 102 may be connected to one another in one or more annular rows around the stent. For example, as shown in FIG. 2, annulus section 140 may have two annular rows of complete cells 112, with the cells in one annular row offset by one-half cell width in the circumferential direction from the cells in the other annular row. Aortic section 142 and transition section 141 may each have one or more annular rows of complete or partial cells 112. The cells in aortic section 142 may be larger than the cells in annulus section 140 so as to better enable prosthetic valve 100 to be positioned within the aortic annulus without the structure of stent 102 interfering with blood flow to the coronary arteries. At least partly due to the shape of cells 112, stent 102 elongates in the direction of longitudinal axis L as the cells collapse when the stent transitions from the expanded condition to the collapsed condition, and shortens in the direction of longitudinal axis L as the stent transitions from the collapsed condition to the expanded condition.

Stent 102 may include one or more retaining elements 118 at outflow end 132, the retaining elements being sized and shaped to cooperate with retaining structures provided on a deployment device (not shown). Stent 102 may also include a plurality of commissure attachment features 116 for mounting the leaflet commissures of the valve assembly to the stent. As can be seen in FIG. 2, each commissure attachment feature 116 may lie at the intersection of four cells 112, two of the cells being adjacent one another in the same annular row, and the other two cells being in different annular rows and lying in end-to-end relationship. Commissure attachment features 116 may be positioned entirely within annulus section 140 or at the juncture of annulus section 140 and transition section 141, and may include one or more eyelets or apertures which facilitate the suturing of the leaflet commissures to stent 102. Stent 102 may be formed as a unitary structure, for example, by laser cutting or etching a tube of a superelastic and/or shape-memory metal alloy, such as a nickel-titanium alloy of the type sold under the designation nitinol. It should be understood that stent 102 may include other forms of commissure attachment features, or may omit commissure attachment features 116, with the prosthetic leaflets being attached to the stent via other mechanisms, such as direct suturing or via intermediary attachment panels.

Prosthetic heart valve 100 includes a valve assembly 104 which may be positioned entirely in the annulus section 140 of stent 102. Valve assembly 104 includes a plurality of leaflets 108 that collectively function as a one way valve by coapting with one another, and a cuff 106 positioned on the luminal surface of stent 102 surrounding leaflets 108. Although cuff 106 is shown in FIG. 2 as being disposed on the luminal or inner surface of annulus section 140, the cuff may be disposed on the abluminal or outer surface of the annulus section, or may cover all or part of either or both of the luminal and abluminal surfaces of the annulus section. As prosthetic heart valve 100 is intended to replace the aortic valve (which ordinarily is a tri-leaflet valve), it is shown in FIG. 2 with three leaflets 108. Adjacent leaflets 108 join one another at leaflet commissures. Each of the leaflet commissures may be sutured to a respective one of the three commissure attachment features 116. Between the leaflet commissures, each leaflet 108 may be sutured to stent 102 and/or to cuff 106 along a leaflet belly B, indicated with broken lines in FIG. 2. Leaflets 108 may be joined to stent 102 and/or to cuff 106 by techniques known in the art other than suturing. Above belly B, leaflets 108 are free to move radially inward to coapt with one another along their free edges. When prosthetic heart valve 100 is implanted in the native aortic valve annulus, blood flows in an antegrade direction from inflow end 130, past leaflets 108, and toward outflow end 132. This occurs when the pressure in the left ventricle is greater than the pressure in the aorta, forcing leaflets 108 to open. When the pressure in the aorta is greater than the pressure in the left ventricle, leaflets 108 are forced closed and coapt with one another along their free edges, blocking blood from flowing through prosthetic heart valve 100 in a retrograde direction from outflow end 132 to inflow end 130 which allows the left and right coronary arteries to fill and feed blood to the heart muscle. It will be appreciated that prosthetic heart valves according to aspects of the present disclosure may have more or less than the three leaflets 108 and commissure attachment features 116 shown in FIG. 2 and described above.

In operation, prosthetic heart valve 100 may be used to replace a native heart valve, such as the aortic valve; a surgical heart valve; or a heart valve that has undergone a surgical procedure. Prosthetic heart valve 100 may be delivered to the desired site (e.g., near the native aortic annulus) using any suitable delivery device (not shown). During delivery, prosthetic heart valve 100 is disposed inside the delivery device in the collapsed condition. The delivery device may be introduced into the patient using any known percutaneous procedure, such as a transfemoral, transapical, transvenous, or transseptal delivery procedure. Once the delivery device has reached the target site, the user may deploy prosthetic heart valve 100. Upon deployment, prosthetic heart valve 100 expands into secure engagement within the native aortic annulus. When prosthetic heart valve 100 is properly positioned inside the heart, it works as a one-way valve, allowing blood to flow in one direction and preventing blood from flowing in the opposite direction.

The descriptions of surgical heart valve 10 and collapsible prosthetic heart valve 100 are for context only. Thus, the leaflet materials described herein may be used in surgical heart valves that are similar to surgical heart valve 10 or surgical heart valves that are very different therefrom. Similarly, the presently disclosed leaflet materials may be used in collapsible prosthetic heart valves that are similar to prosthetic heart valve 100, or prosthetic heart valves that are very different therefrom, such as heart valves having a balloon-expandable stent, heart valve that do not have an aortic section, heart valves intended to replace other cardiac valves, such as the mitral valve, etc. Therefore, the descriptions herein of surgical heart valve 10 and collapsible prosthetic heart valve 100 should in no way be considered as limiting the features and applications of the leaflet materials disclosed herein.

Figure 3:
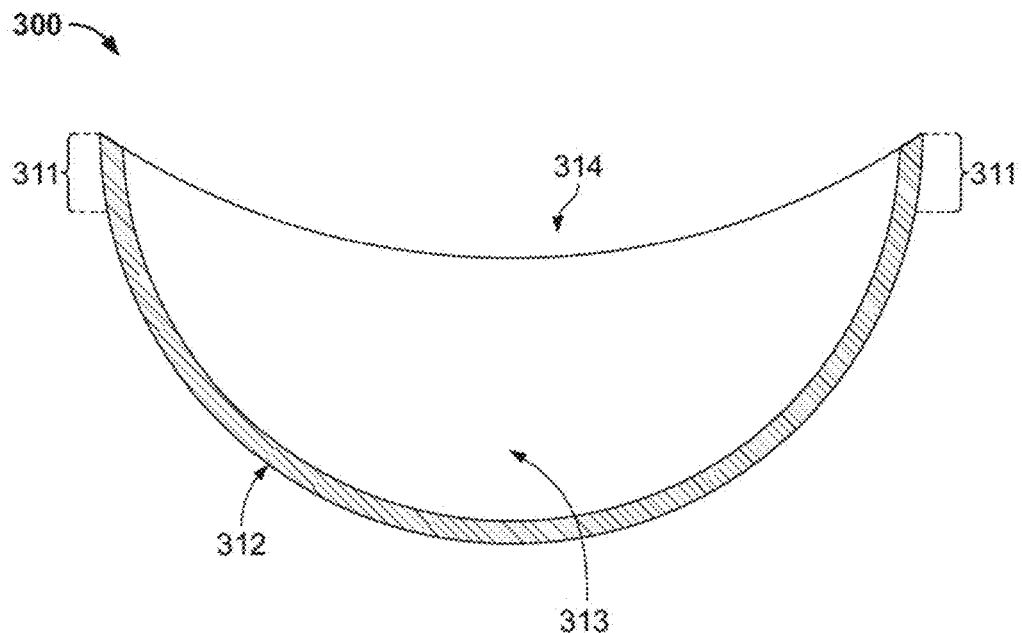
FIG. 3 is a highly schematic illustration of a leaflet, identifying the pertinent regions of the leaflet.

FIG. 3 is a schematic drawing of a leaflet 300 and the pertinent regions of the leaflet 10 as are known in the art. The leaflet 300 includes regions 311 that form commissures with adjacent leaflets, a sewing region 312, a belly 313 and a free edge 314. The commissure regions 311 represent high stress regions of the leaflet at which the leaflet may be mounted to the support structure of the prosthetic heart valve, such as commissure attachment features 116 of prosthetic heart valve 100. The leaflet may also attach to the support structure at the sewing region 312.

Figure 4:
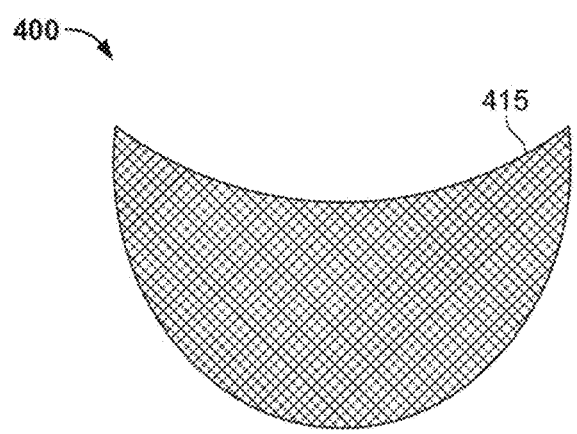
FIG. 4 is a highly schematic plan view of a mesh substrate for a leaflet according to an embodiment of the present disclosure.

In one embodiment, a leaflet 400 may include a mesh substrate, such as the mesh substrate 415 shown in FIG. 4. The mesh substrate may be formed of overlapping wires of a biocompatible metal, such as nitinol, stainless steel, Inconel®, titanium, or cobalt chromium alloys such as L605, Elgiloy® or MP35N®. The wire mesh substrate may have a wire density of at least about 5 ppi (pics per inch). In one embodiment, the mesh substrate may have a wire density of at least about 10 ppi (pics per inch). The mesh substrate may be formed of a wire braid. In one particular embodiment, leaflet 400 may include a nitinol mesh substrate in which the nitinol wires have a diameter of between about 0.0001 inches and about 0.010 inches. In a further embodiment, the nitinol wires may have a diameter of between about 0.0005 inches and about 0.001 inches. The leaflets may comprise a first flat mesh of biocompatible metal wire layered on a second flat mesh of biocompatible metal wire. The resulting mesh substrate may have a thickness of between about 0.001 inches and 0.020 inches. The first flat mesh may be positioned over the entire area of the second flat mesh or only over selected regions of the second flat mesh in which the leaflets experience higher stresses.

Figure 5:
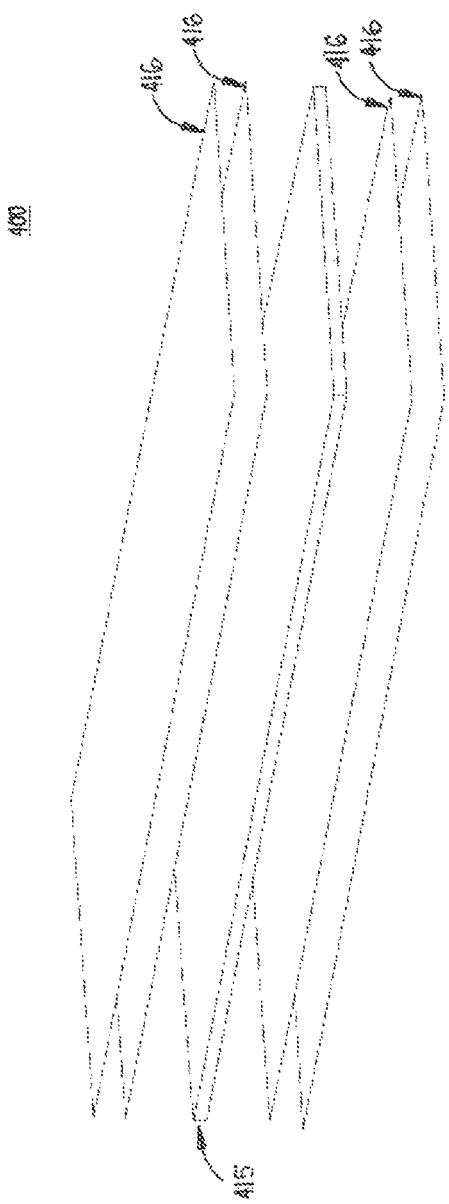
FIG. 5 is a schematic exploded view of the mesh substrate of FIG. 4 coated with layers of polymer according to an embodiment of the present disclosure.

FIG. 5 is an exploded view of the mesh substrate 415 coated with layers of polymer according to an embodiment of the present disclosure. The mesh substrate 415 may be coated with a polymer 416 to produce a nonporous leaflet. The polymer coating may be applied to both sides of the mesh substrate to produce certain desired effects, such as controlling cell attachment, proliferation and activity. The polymer may be applied to the mesh substrate using any mechanism known in the art. Regardless of which technique is used, the mesh substrate may be cut into a leaflet shape prior to coating with a polymer or after the coating process has been completed.

In some embodiments, a polymer may be applied to the mesh substrate in liquid form by spray coating or dip coating. The polymer may be allowed to solidify, such as by cooling, cross-linking, solvent evaporation or another mechanism, to become adhered to the mesh. In other embodiments, a polymer film or sheet may be applied to one or both sides of the mesh substrate. The polymer film or sheet may be adhered to the mesh by gluing, ultrasonic welding or other techniques. The film or sheet may also be heated to soften the polymer so that it flows, with or without the application of pressure, into and throughout the mesh structure. Other techniques for forming the polymer coating on the mesh substrate include electric spinning. Regardless of the technique used to apply the polymer coating, it is desirable that the polymer fill the open spaces in and encapsulate the mesh to create a nonporous leaflet.

The polymer may be applied in a single layer or in multiple layers to one side of the mesh substrate or to each side of the mesh substrate. For example, the spray coating or dip coating processes may be repeated to build up multiple layers of the polymer on the mesh substrate. Where polymer films or sheets are applied to the mesh substrate, multiple such films or sheets may be applied to one or both sides of the mesh substrate as desired (see FIG. 5), and the layers may be fused together with heat and/or pressure to form a continuous structure. If at least one polymer layer is applied to at least a portion of at least one surface of the mesh substrate, at least some benefits, such as impermeability, may be achieved. In some embodiments, 1 to 5 layers of polymer may be applied to one side or to each side of the mesh substrate. In other embodiments, 1 to 10 layers of polymer may be applied to one side or to each side of the mesh substrate. In still other embodiments, up to 20 layers of polymer may be applied to one side or to each side of the mesh substrate. Each layer may have a thickness of between about 2 µm and about 400 µm. Alternatively, the total polymer thickness on one or both sides of the mesh substrate may be between about 25 µm and about 2 mm. The thickness of the various polymer layers need not be the same, and the polymer used to form the layers may be different from one layer to the next, and/or from one side of the mesh substrate to the other side.

In some embodiments, the total thickness of the coated mesh substrate of the disclosure may be between about 50 µm and about 1000 µm, and in other embodiments, may be between about 90 µm and about 800 µm. In still other embodiments, the total thickness of the coated mesh substrate may be between about 100 µm and about 500 µm. It will be appreciated that the thickness desired will be dictated by a balancing of properties and functionality. The number of layers of polymer applied to the mesh substrate will determine the overall thickness of leaflet 400, and therefore can impact the size to which the prosthetic heart valve can be collapsed.

A number of different biocompatible polymers may be used to coat the mesh substrate. In some embodiments, the polymer may comprise a polyolefin, such as a low or high molecular weight polyolefin. In one embodiment, the polyolefin may be an ultra-high molecular weight polyolefin. Polyolefins including, without limitation, polytetrafluoroethylene ("PTFE"), polyethylene, or polypropylene may be used. Other polymers which may be used include polyurethanes, acrylics, polyesters, polyamides, polyimides, vinyl acetates, alkyds, epoxies, silanes, siloxanes, and the like. Homo- and co-polymers of these materials may also be used. Additionally, blends of polymers may be used to form the polymer layers. If more than one polymer is used to coat the mesh substrate, the different polymers may be applied as discrete layers, or blends of two or more polymers may be applied in one or more layers.

In a variant of the embodiment described above, one or more perforated sheets or foils may be substituted for the mesh substrate. One embodiment may employ nitinol sheets or foils, although sheets or foils of other biocompatible metals having the desired strength and flexibility may be used. A metal foil is thinner than a metal sheet, and therefore can form a leaflet with a thinner profile. Thus, while a sheet of nitinol may have a thickness of between about 50 µm and about 500 µm, a nitinol foil may have a thickness of about 25 µm. The nitinol substrate may be provided as a single sheet or multiple sheets of the same thickness or different thicknesses layered on one another to achieve the desired thickness.

In some embodiments, the sheet or foil may be perforated by laser cutting holes therein. The laser cutting may be performed by using a standard nd:YAG laser or fiber lasers. The laser cutting apparatus may include a motion controlled flat bed under the laser. A toolpath file may include the information of the desired pattern. The tool path file may be programed into the laser cutting apparatus and the laser may cut the desired pattern based on the toolpath file. In other embodiments, the sheet or foil may be perforated by etching using photolithography methods known in the art. The etching may be performed by either dry or wet etching. To perforate the sheet or foil by etching, a mask with the desired pattern is placed on the top surface of the sheet or foil. A chemical agent is then applied and reacts with exposed areas of the top surface of the sheet or foil to form perforations in the desired pattern. The desired pattern may include patterns of circular holes, patterns of square diamond holes, patterns of rectangular diamond holes or patterns of slots. In yet other embodiments, the sheet or foil may be perforated by stamping or electrical discharge machining (EDM). It will be appreciated that the number of perforations, their size, their density, and their location may be dictated by a balancing of properties, including, but not limited to, leaflet flexibility and durability. The perforations may appear sporadically throughout the sheet or foil or may form a predetermined pattern, including, but not limited to, a web pattern. Further, a greater number of perforations may be formed in areas in which greater flexibility is desired, and fewer perforations may be formed in areas where greater strength and less flexibility is desired. The sheet or foil may be cut into a leaflet shape before or after forming the perforations therein.

The perforated sheet or foil may be coated using any of the polymers and coating processes described above for coating the mesh substrate. In some embodiments, the total thickness of the coated sheet or foil may be between about 30 µm and about 800 µm, and in other embodiments, may be between about 50 µm and about 600 µm. In still other embodiments, the total thickness of the coated sheet or foil may be between about 75 µm and about 250 µm. It will be appreciated that the use of a sheet or foil as the substrate generally produces a leaflet that is thinner than the leaflet produced using a mesh as the substrate. However, the desired thickness of the leaflet will be dictated by a balancing of properties and functionality. As with the mesh substrate embodiment described above, the number of layers of polymer applied to the sheet or foil will determine the overall thickness of leaflet 400, and therefore can impact the size to which the prosthetic heart valve can be collapsed.

In an additional embodiment of the disclosure, a leaflet may be composed of a fine wire or fabric mesh, wherein the wire or fabric mesh is uncoated. The fine wire forming the mesh may be composed of a metal, preferably a biocompatible metal. Examples of metals that may be used include nitinol, Inconel®, titanium, stainless steel or cobalt chromium alloys such as L605, Elgiloy® or MP35N®. The mesh may have a high wire density so as to act similarly to a fabric. The fine wire may be woven, braided or knitted to create a fabric or mesh that is fine enough to minimize back flow through the prosthetic heart valve and promote tissue ingrowth. The density of the mesh may be adjusted, and often reduced, to promote tissue ingrowth. The mesh may have a wire density of at least about 10 ppi (pics per inch). The leaflet may include a nitinol mesh substrate in which the wires have a diameter of between about 0.0001 inches and about 0.010 inches. The leaflets may comprise a first flat mesh of biocompatible metal wire or fabric mesh layered on a second flat mesh of biocompatible metal wire or fabric mesh. The resulting mesh substrate may have a thickness of between about 0.001 inches and 0.020 inches. The first flat mesh may be positioned over the entire area of the second flat mesh, or only over selected regions of the second flat mesh in which the leaflets experience higher stresses.

Figure 6:
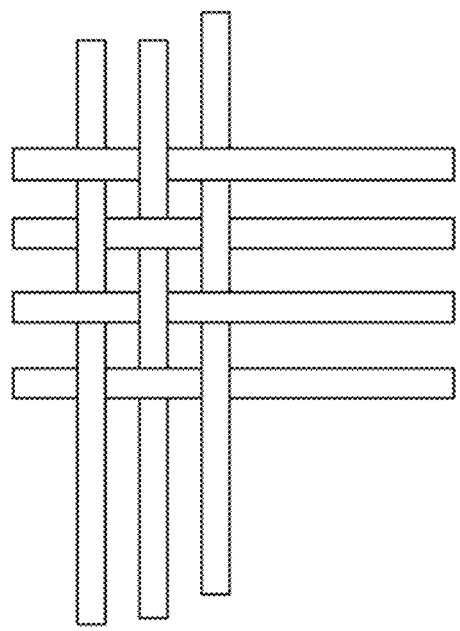
FIG. 6 is an enlarged view of a plain weave pattern.
Figure 7:
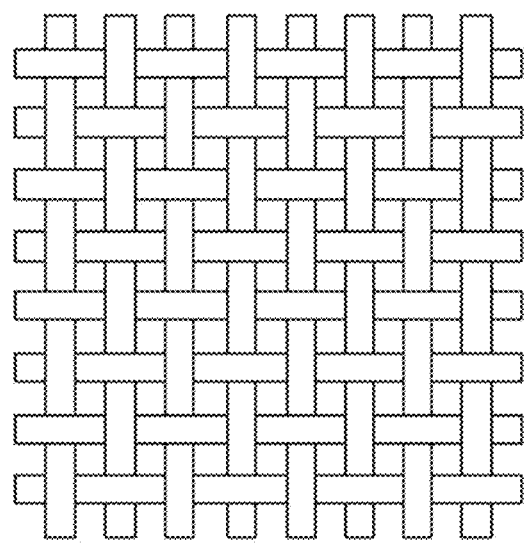
FIG. 7 is a plan view of a plain weave pattern.
Figure 8:
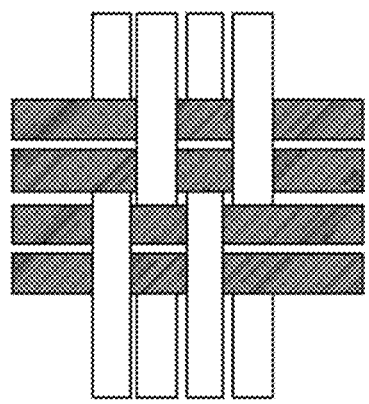
FIG. 8 is a plan view of a warp rib weave pattern.
Figure 9:
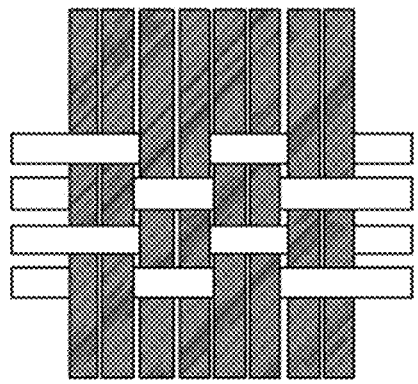
FIG. 9 is a plan view of a weft rib weave pattern.
Figure 10:
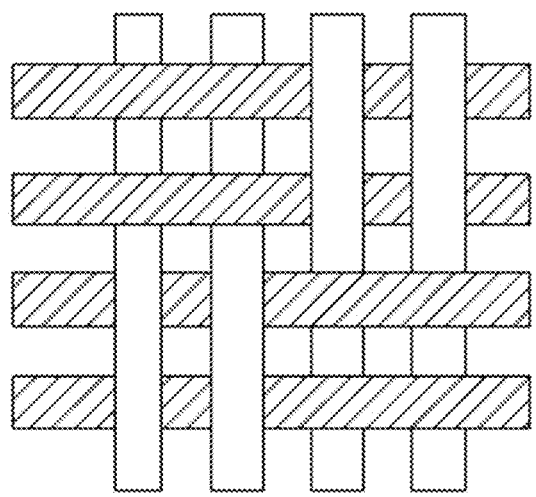
FIG. 10 is a plan view of a basket weave pattern.
Figure 11:
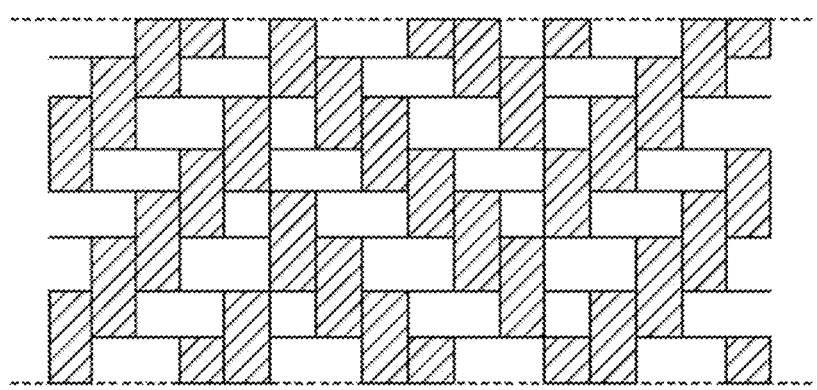
FIG. 11 is a plan view of a herringbone weave pattern.
Figure 12:
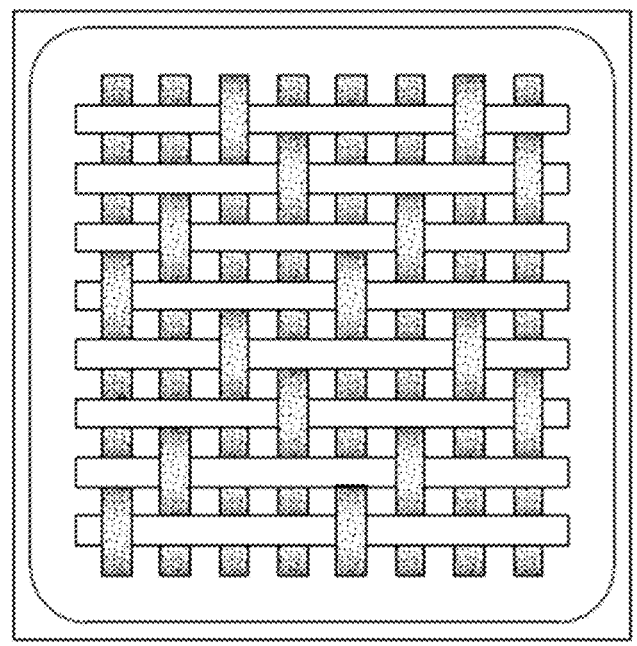
FIG. 12 is a plan view of a satin weave pattern.
Figure 13:
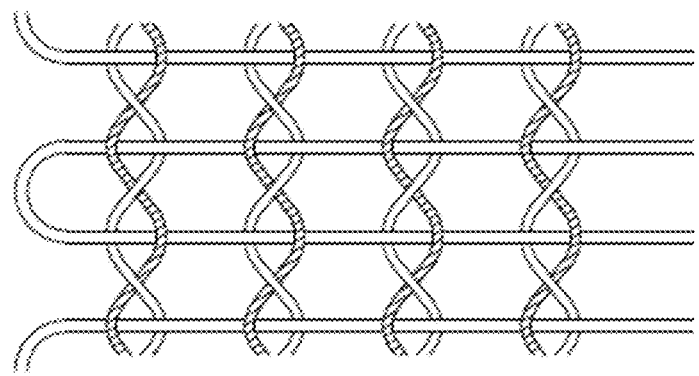
FIG. 13 is a plan view of a leno weave pattern.
Figure 14:
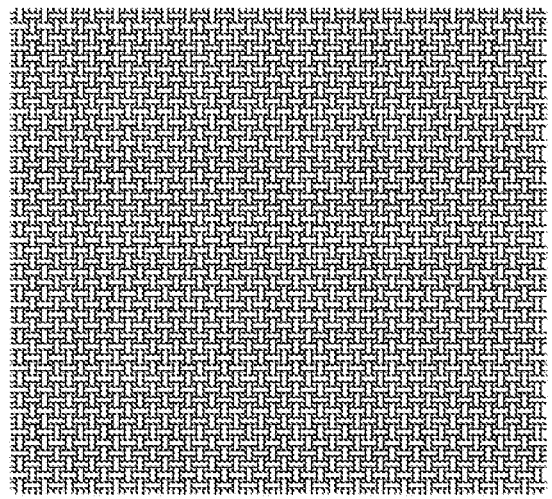
FIG. 14 is a plan view of a twill weave pattern.

FIGS. 6 to 17 illustrate the various weaving and knitting techniques that may be used to form the metal fabric or mesh. The fabric or mesh may be formed by interlacing one, two or more fine strands, which can be accomplished in several ways. Some of the methods for interlacing two or more strands include weaving, knitting, braiding, plaiting, electro spinning, 3-D printing or entangling the strands (mechanically, thermally, chemically, etc.) through felting, bonding or lamination. Woven fabrics and meshes can be fabricated through various techniques. As used herein in connection with the various weaving techniques, "filling" or "weft" refers to strands that extend along the width of the fabric, while "warp" refers to strands that extend along the length of the fabric. A plain weave, shown in FIGS. 6 and 7, is the simplest weaving method in which a single filling strand is passed over and under each warp strand, with the pattern in adjacent rows alternating. (Plain weave, Encyclopaedia Brittanica, Dec. 17, 2010, https://www.britannica.com/technology/plain-weave accessed on Oct. 11, 2019.) One derivative of the plain weave is the rib weave, in which two or more adjacent rows of the filling strand are passed in the same pattern over and under each warp strand. (Watson, Kate Heintz et al., *Textiles and Clothing*, 1907, Home Economics Association, p. 77.) Two versions of the rib weave may also be used, the warp rib weave and the weft rib weave, shown in FIGS. 8 and 9. The warp rib weave produces a rib or cord effect in the weft direction, while the weft rib weave produces a rib or cord effect in the warp direction. (*Difference between Warp Rib Weave and Weft Rib Weave*, Define Textile, 2019, http://www.definetextile.com/2013/05/difference-between-warp-rib-weave-and.html, accessed on Oct. 23, 2019.) Another derivative of the plain weave is a basket weave, in which double or triple strands run in both the filling and warp directions. (Watson at p. 77.) That is, in a basket weave, shown in FIG. 10, two or more adjacent rows of the filling strand are passed in the same pattern over and under two or more adjacent rows of the warp strand. Another weaving technique that can be used to fabricate a fabric or mesh is the twill weave, shown in FIG. 14. The twill weave is known for producing a diagonal pattern when the filling strands are woven over and under two or more adjacent warp yarns. (Twill weave, 2019, https:/www.dictionary.com/browse/twill-weave, accessed on Oct. 11, 2019.) A version of the twill weave includes the herringbone weave, shown in FIG. 11, which resembles a broken zigzag or the bones of a fish. (*What is a Herringbone Weave?*, Shirts of Holland B.V., 2019, https://sleeve7.com/blog/what-is-a-herringbone-weave/, accessed on Oct. 11, 2019.) Another basic weaving technique is the satin weave which produces a soft, smooth and lustrous face without the appearance of a pattern. (*Basic Weaves*, Cotton Incorporated, 2019, https://www.cottonworks.com/topic s/sourcing-manufacturing/weaving/the-art-of-weaving-basic-weaves/, accessed on Oct. 11, 2019.) An example of the satin weave is shown in FIG. 12.

Figure 15:
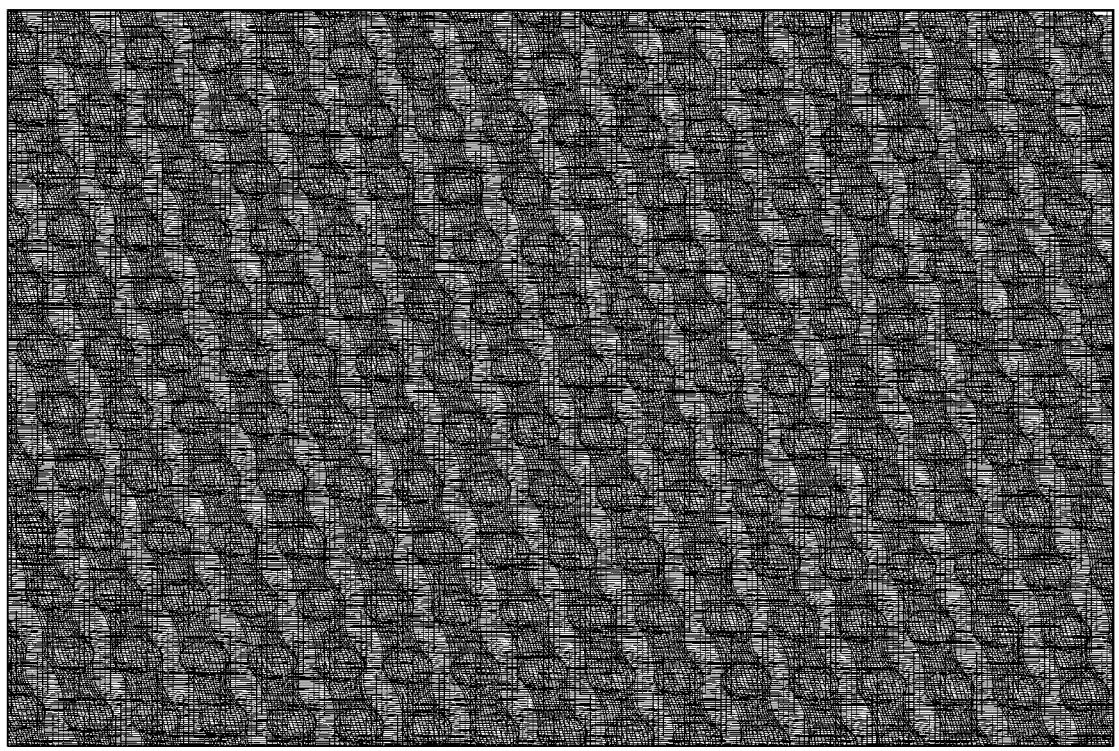
FIG. 15 is a plan view of a waffle weave pattern.
Figure 16:
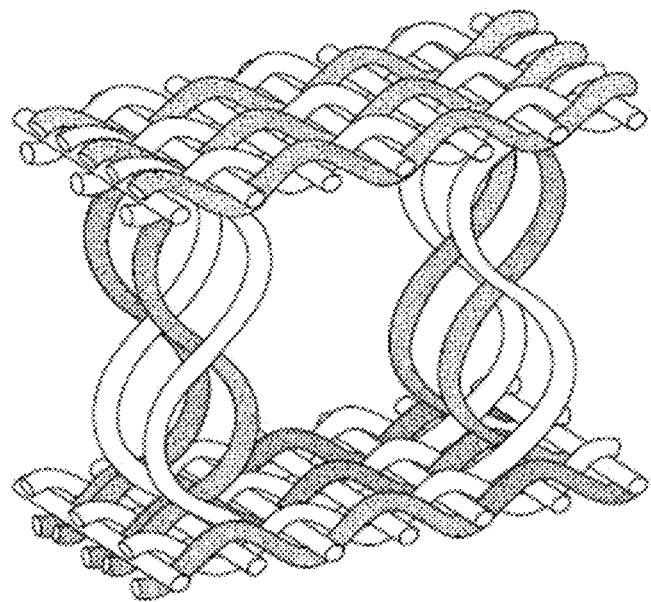
FIG. 16 is a perspective view of a pile weave pattern.

Additional weaving techniques can be used to form the fabrics or meshes as well. One additional weaving technique is the leno weave, shown in FIG. 13, a principal of interweaving in which some of the warp ends do not lie parallel to one another, but are twisted partly around other ends. (*Leno Weaves*, Serial 512. Ed. 1., International Textbook Co., https://www2.cs.arizona.edu/patterns/weaving/monographs/ics512.pdf, accessed on Oct. 11, 2019.) Another weaving technique is the Bedford cord, in which the weaves produce longitudinal warp lines in the fabric with fine sunken lines in between. (*Bedford Cords*, TextileSchool4U.Blogspot.com, 2013, http://textileschool4u.blogspot.com/2013/12/bedford-cords.html, accessed on Oct. 11, 2019.) A waffle weave as shown in FIG. 15 can also be used by weaving the strands into a pattern resembling a honeycomb. (Honeycomb, The Free Dictionary, https://www.thefreedictionary.com/waffle+weave, accessed on Oct. 11, 2019.) Also usable is a pile weave, which incorporates a loop pattern into the weave to produce a fabric with a raised, dense surface. (Adam Augustyn, Weaving, 2008, https://www.britannica.com/technology/weaving#ref290551, accessed on Oct. 11, 2019.) An example of a pile weave is shown in FIG. 16. A jacquard weave is another available technique which produces a fabric or mesh on a special loom because of the complex woven-in designs. (Id.) Similarly, a dobby weave requires a special loom attachment to incorporate small, geometric, textured, repeated woven-in designs. (Id.) Tapestry weaving, in which the warp threads do not show at all, is another available technique. (*Tapestry Weaving Basics*, 2019, https://www.mirrixlooms.com/pages/tapestry-weaving-basics, accessed on Oct. 11, 2019.) An additional weaving technique is the double cloth weave, in which the fabric or mesh is made of two or more sets of warp strands and one or more sets of weft or filling strands that are interconnected to form a two-layered fabric or mesh. (Double Cloth, Mar. 20, 2019, https://en.wikipedia.org/wiki/Double_cloth#cite_ref-text_2-0, accessed on Oct. 11, 2019.) Other weaves that may be suitable include sateen weaves, crepe weaves, lappet weaves, striped weaves, and checkered weaves.

Figure 17:
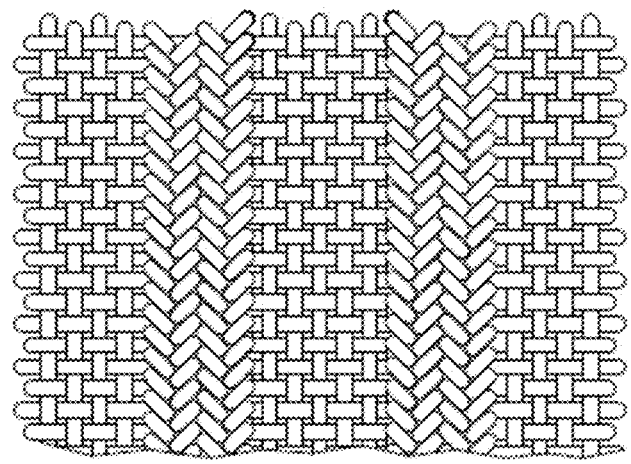
FIG. 17 is a plan view of single knit and purl knit patterns.

A variety of knitting techniques may also be used to produce metal fabrics or meshes for the leaflets of prosthetic heart valves. Knitting involves interlacing loops of at least one strand. The main fabrics and meshes produced by knitting are weft knits, specialized weft knits and warp knits. A weft knit fabric or mesh can either be a single knit or a double knit. A single knit fabric or mesh is produced by one set of needles, while a double knit fabric or mesh is produced by two sets of needles. (Random House Kernerman Webster's College Dictionary, 2010, K Dictionaries Ltd.) The most common example of a single knit fabric is a single jersey. The most common double knit fabrics include rib knit, purl knit, interlock knit, cable fabric, bird's eye, cardigans, Milano ribs and pointelle. Examples of single knit and purl knit fabrics are shown in FIG. 17. The rib knit fabric is known for having a ribbed pattern. (Rib-knit, Merriam-Webster, 2019, https://www.merriam-webster.com/dictionary/rib-knit, accessed on Oct. 11, 2019.) A fabric or mesh with an interlock knit is a variation of the rib knit fabric with closely interlocking stitches providing the tightest weave. Fabrics or meshes produced with a specialized weft knit include intarsia, jacquard jerseys, knitted terry, knitted velour, sliver knit, fleece and French terry. There are two types of warp knitting commonly used, raschel and tricot. (Warp knitting, Sep. 15, 2019, https://en.wikipedia.org/wiki/Warp_knitting, accessed on Oct. 11, 2019.) Raschel knitting produces fabrics or meshes by using latch needles, while tricot knitting uses a bearded needle. (Id.)

According to another embodiment of the disclosure, a leaflet may be composed of natural tissue. The natural tissue may be composed of bovine, porcine, ovine or equine pericardial tissue. The natural tissue may be in the form of a sheet or cut into the shape of the leaflet. The tissue may be cut by various cutting techniques including mechanical methods, for example using a scissor or a blade. The tissue may also be cut by other techniques, including, for example, cautery, or chemical, laser, ultrasonic, or water jet cutting.

The natural tissue may be preserved using plastination preservation. In plastination preservation, the water and fat in the tissue is replaced with a biocompatible polymer. Polymers that may be used include, without limitation, ultra-high molecular weight polyolefin, such as polyethylene; silicone rubber; polyurethane; polypropylene; or an epoxy resin. Other synthetic polymer materials may also be used, including, for example, polyester. The natural tissue may be subjected to the plastination preservation process before or after the tissue has been cut into tissue shapes. The plastination preservation process may include fixing the tissue as is known in the art. After fixation, water and soluble fats are dissolved from the tissue in a first bath. The first bath may include acetone. The bath may be chilled, which may cause the water from the tissue to be drawn out and replaced with acetone. When most or all of the water has been drawn out from the tissue, the tissue is removed from the acetone bath and placed in a second bath. The second bath may include any of the biocompatible polymers just mentioned above in a liquid form, as well as combinations of those polymers. The tissue in the second bath may be placed under a vacuum, wherein the acetone may boil at a low temperature. When the acetone boils, it begins to vaporize, leaving the cells. The resulting voids in the tissue are then replaced with the liquid polymer. The plastination preservation process may take several days to complete from beginning to end. By using plastination preservation, the function and durability of the leaflet may be optimized.

To summarize the foregoing, one embodiment of the disclosure provides a prosthetic heart valve, including a support structure; and a valve assembly disposed within the support structure, the valve assembly including a plurality of leaflets, wherein each leaflet is formed from a composite material, the composite material including a metal substrate having a plurality of openings, and a polymer coated on the metal substrate; and/or
  the metal substrate may be a mesh; and/or
  the mesh may be formed of metal wire having a diameter of between about 0.0005 inches and about 0.010 inches; and/or
  the mesh may be formed of a first flat mesh of biocompatible metal wire layered on a second flat mesh of biocompatible metal wire; and/or
  the metal substrate may be a perforated sheet; and/or
  the perforated sheet may include holes formed by a method selected from the group consisting of laser cutting, etching, stamping and electrical discharge machining ("EDM"); and/or
  the polymer may be selected from the group consisting of ultra-high molecular weight polyolefin, polytetrafluoroethylene, polyester or combinations thereof; and/or
  the polymer may fill the plurality of openings in the metal substrate; and/or
  the support structure may be collapsible for insertion into a patient and expandable for use; and/or
  the support structure may be substantially rigid; and/or
  the polymer may be coated on first and second opposite surfaces of the metal substrate; and/or
  the polymer may be coated on the metal substrate in a plurality of layers.

Another embodiment of the disclosure provides a method for fabricating any of the prosthetic heart valves described in the immediately preceding paragraph.

A further embodiment of the disclosure provides a prosthetic heart valve, including a support structure; and a valve assembly disposed within the support structure, the valve assembly including a plurality of leaflets, wherein each leaflet is formed from a metal body having a plurality of openings, the metal body including a fine wire that is woven, knitted or braided to form a mesh; and/or
  the fine wire may be uncoated; and/or
  the mesh may have a wire density of at least 10 ppi (pics per inch); and/or
  the support structure may be collapsible for insertion into a patient and expandable for use; and/or
  the support structure may be substantially rigid; and/or
  the polymer may be coated on first and second opposite surfaces of the metal substrate; and/or
  the polymer may be coated on the metal substrate in a plurality of layers.

Yet another embodiment of the disclosure provides a method for fabricating any of the prosthetic heart valves described in the immediately preceding paragraph.

A still further embodiment of the disclosure provides a prosthetic heart valve, including a support structure; and a valve assembly disposed within the support structure, the valve assembly including a plurality of leaflets, wherein each leaflet is formed from natural tissue that has been subjected to a plastination preservation process; and/or
  the natural tissue may include a polymer as a result of the plastination preservation process; and/or
  the polymer may be selected from the group consisting of ultra-high molecular weight polyolefin, polyester, silicone rubber, polyurethane, polypropylene, epoxy resin or combinations thereof; and/or
  the support structure may be collapsible for insertion into a patient and expandable for use; and/or
  the support structure may be substantially rigid.

Still another embodiment of the disclosure provides a method for fabricating any of the prosthetic heart valves described in the immediately preceding paragraph.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
  a support structure; and
  a valve assembly disposed within the support structure, the valve assembly including a plurality of leaflets,
  wherein each leaflet is formed from a composite material, the composite material including a metal substrate in the form of a mesh having a plurality of openings, and a polymer coated on the metal substrate, the mesh being formed of a first flat mesh of biocompatible metal wire layered on a second flat mesh of biocompatible metal wire without a layer of the polymer between the first flat mesh and the second flat mesh.

2. The prosthetic heart valve according to claim 1, wherein the mesh is formed of metal wire having a diameter of between about 0.0001 inches and about 0.010 inches.

3. The prosthetic heart valve according to claim 1, wherein the polymer is selected from the group consisting of ultra-high molecular weight polyolefin, polytetrafluoroethylene, polyethylene, polypropylene, polyurethane, acrylic, polyester, polyimides, vinyl acetates, alkyds, epoxies, silanes, siloxanes or combinations thereof.

4. The prosthetic heart valve according to claim 1, wherein the polymer fills the plurality of openings in the metal substrate.

5. The prosthetic heart valve according to claim 1, wherein the support structure is collapsible for insertion into a patient and expandable for use.

6. The prosthetic heart valve according to claim 1, wherein the support structure is rigid.

7. The prosthetic heart valve according to claim 1, wherein the polymer is coated on first and second opposite surfaces of the metal substrate.

8. The prosthetic heart valve according to claim 7, wherein the polymer is coated on the metal substrate in a plurality of layers.

9. The prosthetic heart valve according to claim 1, wherein the first flat mesh of biocompatible metal wire is positioned over only selected regions of the second flat mesh of biocompatible metal wire.

10. A prosthetic heart valve, comprising:
a support structure; and
a valve assembly disposed within the support structure, the valve assembly including a plurality of leaflets,
wherein each leaflet is formed from a metal body having a plurality of openings, the metal body including a fine wire that is woven, knitted or braided to form a first flat mesh of biocompatible metal wire layered over a second flat mesh of biocompatible metal wire, the first flat mesh being positioned over only selected regions of the second flat mesh, and the metal body being devoid of a tissue or polymer coating.

11. The prosthetic heart valve according to claim 10, wherein the mesh has a wire density of at least 10 ppi (pics per inch).

12. The prosthetic heart valve according to claim 10, wherein the support structure is collapsible for insertion into a patient and expandable for use.

13. The prosthetic heart valve according to claim 10, wherein the support structure is rigid.

\* \* \* \* \*